United States Patent
Roteliuk et al.

(10) Patent No.: US 8,764,668 B2
(45) Date of Patent: *Jul. 1, 2014

(54) DISPOSABLE BLOOD PRESSURE TRANSDUCER AND MONITOR INTERFACE

(75) Inventors: Luchy Roteliuk, Lake Forest, CA (US); Weldon Dean West, Mission Viejo, CA (US); Douglas Meyer, Jr., Tustin, CA (US); Luong N. Phan, San Clemente, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 1263 days.

This patent is subject to a terminal disclaimer.

(21) Appl. No.: 12/558,160

(22) Filed: Sep. 11, 2009

(65) Prior Publication Data

US 2010/0056932 A1 Mar. 4, 2010

Related U.S. Application Data

(63) Continuation of application No. 10/888,332, filed on Jul. 8, 2004, now Pat. No. 7,604,602.

(51) Int. Cl.
*A61B 5/021* (2006.01)
*A61B 5/0205* (2006.01)
*A61B 5/022* (2006.01)
*A61B 5/023* (2006.01)
*A61B 5/0235* (2006.01)
*A61B 5/029* (2006.01)

(52) U.S. Cl.
USPC ........... 600/486; 600/481; 600/483; 600/485; 600/488; 600/489; 600/490; 600/491; 600/492; 600/493; 600/494; 600/495; 600/496; 600/497; 600/498; 600/499; 600/526; 600/561

(58) Field of Classification Search
USPC ......... 600/301, 481, 483, 485, 486, 488–499, 600/526, 561
See application file for complete search history.

(56) References Cited

U.S. PATENT DOCUMENTS

| | | | |
|---|---|---|---|
| 3,798,463 A | 3/1974 | Ikeguchi et al. | |
| 4,010,387 A | 3/1977 | Akamatsu | |
| 4,446,715 A | 5/1984 | Bailey | |
| 4,603,574 A * | 8/1986 | Norman | 73/1.57 |
| 4,680,731 A | 7/1987 | Izumi et al. | |
| 4,760,730 A * | 8/1988 | Frank et al. | 73/1.59 |
| 4,825,876 A | 5/1989 | Beard | |

(Continued)

FOREIGN PATENT DOCUMENTS

| | | |
|---|---|---|
| JP | 406334670 A | 12/1994 |
| JP | 2002290418 A | 10/2002 |

*Primary Examiner* — Jacqueline Cheng
*Assistant Examiner* — Puya Agahi
(74) *Attorney, Agent, or Firm* — Michael Crapenhoft (57) ABSTRACT

A medical blood pressure transducer that provides an identifier to a monitor that conveys characteristics of the transducer. The monitor can use the information to decide whether to function, or in calibration of the system. The transducer may be part of a disposable blood pressure monitoring system, and may include two transducers closely-spaced to provide two separate but identical outputs. In this way, the transducer may be connected to both a patient monitor and a cardiac output monitor at the same time measurements from a single line can be simultaneously supplied to two separate monitoring devices (for example a patient monitor and a cardiac output monitor). The identifier for the transducer may be circuitry, specifically a resistance/capacitance (RC) combination that possesses a characteristic time constant.

7 Claims, 6 Drawing Sheets

(56) References Cited

U.S. PATENT DOCUMENTS

| | | | |
|---|---|---|---|
| 5,105,820 A | 4/1992 | Moriuchi et al. | |
| 5,181,858 A | 1/1993 | Matz et al. | |
| 5,267,566 A * | 12/1993 | Choucair et al. | 600/488 |
| 5,400,267 A * | 3/1995 | Denen et al. | 702/59 |
| 5,405,269 A | 4/1995 | Stupecky | |
| 5,444,776 A | 8/1995 | Sheets et al. | |
| 5,540,100 A | 7/1996 | von Berg | |
| 5,568,610 A | 10/1996 | Brown | |
| 5,772,466 A | 6/1998 | Morin et al. | |
| 6,171,264 B1 * | 1/2001 | Bader | 600/595 |
| 6,283,775 B1 | 9/2001 | Shupe et al. | |
| 6,431,892 B1 | 8/2002 | Shoupe et al. | |
| 6,651,175 B1 | 11/2003 | Slama | |
| 6,661,236 B2 | 12/2003 | Goers et al. | |
| 6,676,600 B1 * | 1/2004 | Conero et al. | 600/438 |
| 7,258,688 B1 * | 8/2007 | Shah et al. | 606/34 |
| 2001/0029315 A1 * | 10/2001 | Sakurai et al. | 600/101 |
| 2002/0107538 A1 * | 8/2002 | Shibata et al. | 606/169 |
| 2002/0199111 A1 | 12/2002 | Clark et al. | |
| 2003/0048212 A1 | 3/2003 | Libove | |
| 2003/0141916 A1 | 7/2003 | Conero | |
| 2004/0082866 A1 * | 4/2004 | Mott et al. | 600/486 |
| 2004/0082944 A1 * | 4/2004 | Howell | 606/29 |
| 2004/0243120 A1 * | 12/2004 | Orszulak et al. | 606/34 |
| 2004/0267103 A1 * | 12/2004 | Li et al. | 600/323 |

* cited by examiner

DISPOSABLE BLOOD PRESSURE TRANSDUCER AND MONITOR INTERFACE

RELATED APPLICATION

This application is a continuation of U.S. application Ser. No. 10/888,332 entitled "Disposable Blood Pressure Transducer and Monitor Interface" filed Jul. 8, 2004 which is hereby incorporated herein in its entirety, by reference.

FIELD OF THE INVENTION

The present invention relates generally to pressure transducers for medical use and, more particularly, to a disposable blood pressure transducer and associated monitor interface.

BACKGROUND OF THE INVENTION

When diagnosing and treating various bodily ailments, such as with patients suffering from shock or cardiovascular problems, medical personnel often find it desirable to measure and/or monitor a patient's blood pressure. Advantageously, by measuring and/or monitoring the blood pressure of these and other types of patients, medical personnel are better able to detect blood flow difficulties and other cardiovascular problems at an early stage. As a result, the use of blood pressure measurement and monitoring may increase the likelihood that a patient can be successfully treated and/or provided with needed emergency assistance.

A variety of methods are currently used for measuring and/or monitoring blood pressure. For example, medical personnel frequently use various indirect blood pressure measurement techniques, such as measuring a patient's blood pressure by using a pressure cuff and a stethoscope. In addition, blood pressure measurements are often made using a number of direct measurement and monitoring techniques. Notably, when diagnosing and/or treating critically ill patients, such direct techniques are greatly preferred over any of the indirect techniques. Direct blood pressure measurement and monitoring techniques are generally accurate to within about one percent, and facilitate the continuous monitoring of a patient's blood pressure on a beat-to-beat basis. Direct blood pressure monitoring also enables the rapid detection of a change in cardiovascular activity, and this may be of significant importance in emergency situations.

In direct, or invasive, blood pressure monitoring systems a catheter is inserted into a patient's circulatory system with the end of the catheter having an opening to the blood stream, typically in a major or peripheral blood vessel. First, a needle is inserted into a peripheral blood vessel. For example, if it is desired to monitor arterial blood pressure, the needle may be inserted into the radial artery. If, on the other hand, venous blood pressure is to be monitored, the needle may be inserted into the antecubital, radial, jugular, or subclavian veins. Once the needle is properly inserted, a special catheter is threaded through the needle and into the blood vessel until the tip of the catheter is positioned at the particular point within the body at which it is desired to make the blood pressure measurement. Then, with the catheter in place, the needle may be withdrawn.

An I.V. set attaches to the proximal end of the catheter protruding from the patient so that a solution flows through the catheter and into the patient. The I.V. solution provides a fluid "column" through which pressure pulses are transmitted, and a pressure transducer positioned along the fluid column monitors those pressure pulses. Generally, the pressure transducer consists of a dome that functions as a reservoir for the I.V. fluid. The dome includes a resilient diaphragm that attaches to an electrical transducer. The transducer senses pressure fluctuations in the diaphragm and converts them into electrical signals which then transmit through a cable to a monitor for amplification and display. In modern systems a single silicon chip comprises both the pressure diaphragm and the measuring circuitry of the pressure transducer. Since such silicon chips are cheaply mass-produced, the total cost of pressure transducers is reduced to the extent that the transducer becomes economically disposable. The cable includes a connector so that the transducer and associated portion of the cable can be discarded after use, whereas the mating connector and cable hard-wired to the monitor can be reused. Such disposable blood pressure transducers (DPTs) are the standard of care in the OR, ICU or CCU.

Due to the separable nature of the transducer and monitor, different transducers may be connected to any one monitor, as long as the cable connectors are compatible. However, transducers from different sources may exhibit different performance characteristics and may require specific calibration and/or signal processing or conditioning. Unfortunately, the environments of the OR, ICU or CCU are ill-suited for rapid recognition and registration of disparate components of pressure monitoring systems, and safety concerns necessitate the least amount of such preparation be involved.

Furthermore, pressure data are often required by two separate monitoring devices, such as a patient monitor and a cardiac output monitor, or a patient monitor and an aortic balloon pump. Typically, an arterial line is placed in the patient and a DPT connected to a patient monitor is used for pressure monitoring. Instead of invasively setting up a second arterial line and DPT, the signal from the first DPT may be supplied to a second monitor via the patient monitor. However, this "piggyback" connection may introduce pressure monitoring errors from delays and distortion of the signals.

Despite a relatively mature market for disposable medical pressure transducers, there remains a need for a "smart" transducer that when interfaced with the appropriate monitoring device ensures accuracy. There is also a need for a simpler and more reliable system for transmitting the pressure signal to multiple instruments.

SUMMARY OF THE INVENTION

The present invention provides a pressure monitoring system that facilitates rapid recognition, registration and/or conditioning of a disposable blood pressure transducing device by an associated monitor, and reduces the amount of such preparation involved. Further, the disposable blood pressure transducing device embodies "smart" technology such that an identifier that characterizes the blood pressure transducing device is sensed by a signal receiving device, which allows the signal receiving device to appropriately condition the signal and helps improve safety.

One aspect of the invention is a medical fluid pressure sensing system having a pressure transducing device that comprises a pressure-sensitive transducer and an identifier. The pressure-sensitive transducer is capable of externally measuring fluid pressures and converting those pressures into electrical signals. The identifier characterizes the pressure transducing device. The system further includes a signal receiving device adapted to communicate with the pressure transducing device and capable of sensing the identifier and therefore the characteristics of the pressure transducing device when placed in communication therewith.

In an exemplary system, the pressure transducing device is a fluid pressure transducing device which further comprises a housing having a conduit in which fluid may enter. The pressure-sensitive transducer is mounted in the housing for measuring fluid pressures in the conduit and converting those pressures into electrical signals. Desirably, the fluid pressure transducing device also has an electrical connector connected to the pressure transducer for transmitting the signals. Consequently, the signal receiving device is adapted to physically and electrically communicate with the connector and receive the electrical signals and is capable of sensing the identifier and therefore the characteristics of the fluid pressure transducing device when placed in communication with the connector. In the preferred embodiment, the pressure-sensitive transducer directly senses fluid pressure.

In one embodiment, the identifier introduces an electrical signature to the signals such that the signals and signature can be recognized by the signal receiving device. The electrical signature may be a time- or frequency-based feature. The physical makeup of the identifier may be selected from a group consisting of the following:

a combination of a resistor, a capacitor, and/or an inductor;
a memory chip;
a reference voltage/current;
an electro-magnetic signature;
an active or passive switch which can be electrically, mechanically, optically, or magnetically triggered; and
an optical identifier.

Preferably, the identifier is provided in electrical circuitry. For instance, the electrical circuitry may comprise a resistance/capacitance (RC) combination that possesses a characteristic time constant. In such a configuration, the pressure transducing device may further include an electrical connector in communication with the pressure transducer for transmitting the signals, wherein the connector includes electrical contact pins and a capacitor bridging two of the pins that provides the capacitance in the RC combination. Consequently, the signal receiving device is adapted to physically and electrically communicate with the connector and is capable of sensing the identifier and therefore the characteristics of the pressure transducing device when placed in communication with the connector. The signal receiving device may include decision-making circuitry that will only permit functioning of the system depending on a determination of the time constant. In one desirable embodiment, the decision-making circuitry will only permit functioning of the system if the time constant is within 20% of a reference value.

Another aspect of the present invention is a medical fluid pressure transducing device including a housing having a conduit in which fluid may enter. A pressure-sensitive transducer mounts in the housing for measuring fluid pressures in the conduit and converting those pressures into electrical signals. An electrical connector connects to the pressure transducer for transmitting the signals. An electrical identifier characterizes the type of fluid pressure transducing device. Desirably, the pressure-sensitive transducer directly senses fluid pressure.

The identifier may introduce an electrical signature to the signals that can be recognized by a signal receiving device adapted to communicate with the connector. The electrical signature may be a time- or frequency-based feature. The physical makeup of the identifier may be selected from a group consisting of the following:

a combination of a resistor, a capacitor, and/or an inductor;
a memory chip;
a reference voltage/current; and
an electro-magnetic signature.

Preferably, the electrical identifier comprises a resistance/capacitance (RC) combination that possesses a characteristic time constant. In such a configuration, the connector includes electrical contact pins and the transducer includes a capacitor bridging two of the pins that provides the capacitance in the RC combination. The electrical identifier ideally comprises circuitry on the housing, the transducer, the cable, or the connector.

A still further aspect of the invention is a dual fluid pressure transducing device, comprising an in-dwelling catheter and an external housing connected to the catheter having a conduit in which fluid may enter, the fluid therefore being placed in communication with a lumen of the in-dwelling catheter. Two pressure sensors mount in the housing for measuring fluid pressures in the conduit and converting those pressures into electrical signals. An electrical connector is in communication with each pressure transducer for transmitting the signals.

In the exemplary dual fluid pressure transducing device, the pressure sensors directly sense fluid pressure. The device may further include a stopcock assembly interposed between the housing conduit and the in-dwelling catheter for opening the conduit to the atmosphere and providing a reference pressure in a fluid column defined within the conduit at a particular elevation, the pressures sensed by the two pressure sensors being the same along the fluid column.

In a preferred embodiment, the assembly of one of the pressure sensors and associated connector includes an identifier that characterizes the type of pressure sensor. In such an arrangement, the two connectors may be differently colored. The housing may also include a single snap tab for permitting flow through the conduit and generating a square pressure wave within the fluid in the conduit that can be detected by the two pressure sensors.

The present invention also provides a method of measuring fluid pressure from a location within a patient. The method includes the steps of:

inserting a catheter into a body vessel or cavity;
providing an external housing connected to the catheter having a conduit in which fluid may enter, the fluid therefore being placed in communication with a lumen of the in-dwelling catheter, the housing having at least one fluid pressure sensor mounted therein for measuring fluid pressures in the conduit and converting those pressures into electrical signals; and
transmitting signals representing two measurements of fluid pressure from the at least one fluid pressure sensor to at least one signal receiving monitor.

In a preferred method, there are two fluid pressure sensors, and the signals representing two measurements of fluid pressure derive one from each sensor. An electrical connector may be associated with each fluid pressure sensor, wherein the method further includes connecting the two connectors to different signal receiving monitors.

In a preferred method, the assembly of one of the fluid pressure sensors and associated connector may include an identifier that characterizes the type of pressure sensor. With such a configuration, the method includes detecting the identifier with the monitor and adjusting signal processing accordingly. The signals representing two measurements of fluid pressure may be transmitted to two different signal receiving monitors. In a specific application, the fluid is blood and one monitor is a patient monitor and the other is a cardiac output monitor.

Further understanding of the nature and advantages of the invention will become apparent by reference to the remaining portions of the specification and drawings.

DESCRIPTION OF THE PREFERRED EMBODIMENTS

The present invention provides an improved disposable blood pressure transducing device (DPT) that carries with it an identifier that can be detected by an associated monitor such that the monitor recognizes the characteristics of the device. If the monitor recognizes the type of DPT as compatible, it can proceed with the pressure measurement. Ideally the monitor is calibrated to work best with particular DPTs, and the identifier provides the "signature" for those transducers that are optimal. More generally, the identifier tells the monitor which type of DPT it is receiving signals from and therefore what, if any, signal conditioning is required.

The term "identifier" is used herein to broadly encompass features of the DPTs that can be sensed or otherwise recognized by the monitor. Electrical circuitry is probably the most efficient means to identify a DPT because it can be built in to the existing circuitry and sensed via the DPT connector pins, without need to physically modify the monitor connector. For instance, a resistance/capacitance (RC) combination that possesses a characteristic time constant can be built into the DPT electrical circuit and the monitor can easily be configured to interrogate the DPT connector for that time constant. Other identifiers are listed below and the reader should be cognizant that any of these interfaces between the DPT and monitor may be used.

In the context of the present invention, a blood "pressure transducer" is a sensor capable of sensing or determining a blood pressure, such as the fluid pressure of blood within a line leading out of the body from an arterial catheter, and converting such pressure to a signal that can be communicated to a monitor/display. A number of such blood pressure transducers are known, and none are specifically excluded from the scope of the invention. Blood pressure can be sensed directly (i.e., via direct physical contact with blood) or indirectly (i.e., optically or at a pulse point through the skin). For example, catheter-based fluid pressure transducers in direct contact with arterial blood are presently accepted as standard practice in the OR, ICU or CCU, though less-invasive techniques such as external piezo-electric sensors in contact with the skin are available. It should be understood that the aspect of the invention that permits identification of the particular sensor/transducer by the monitor is not limited to direct or indirect measurement techniques, or to fluid pressure monitoring for that matter. Although blood pressures are the target parameter measured in the exemplary embodiments, certain aspects of the "smart" interface between the transducer and monitor may also be desirable for systems that measure other bodily fluids, such as cerebro-spinal fluid.

Figure 1:
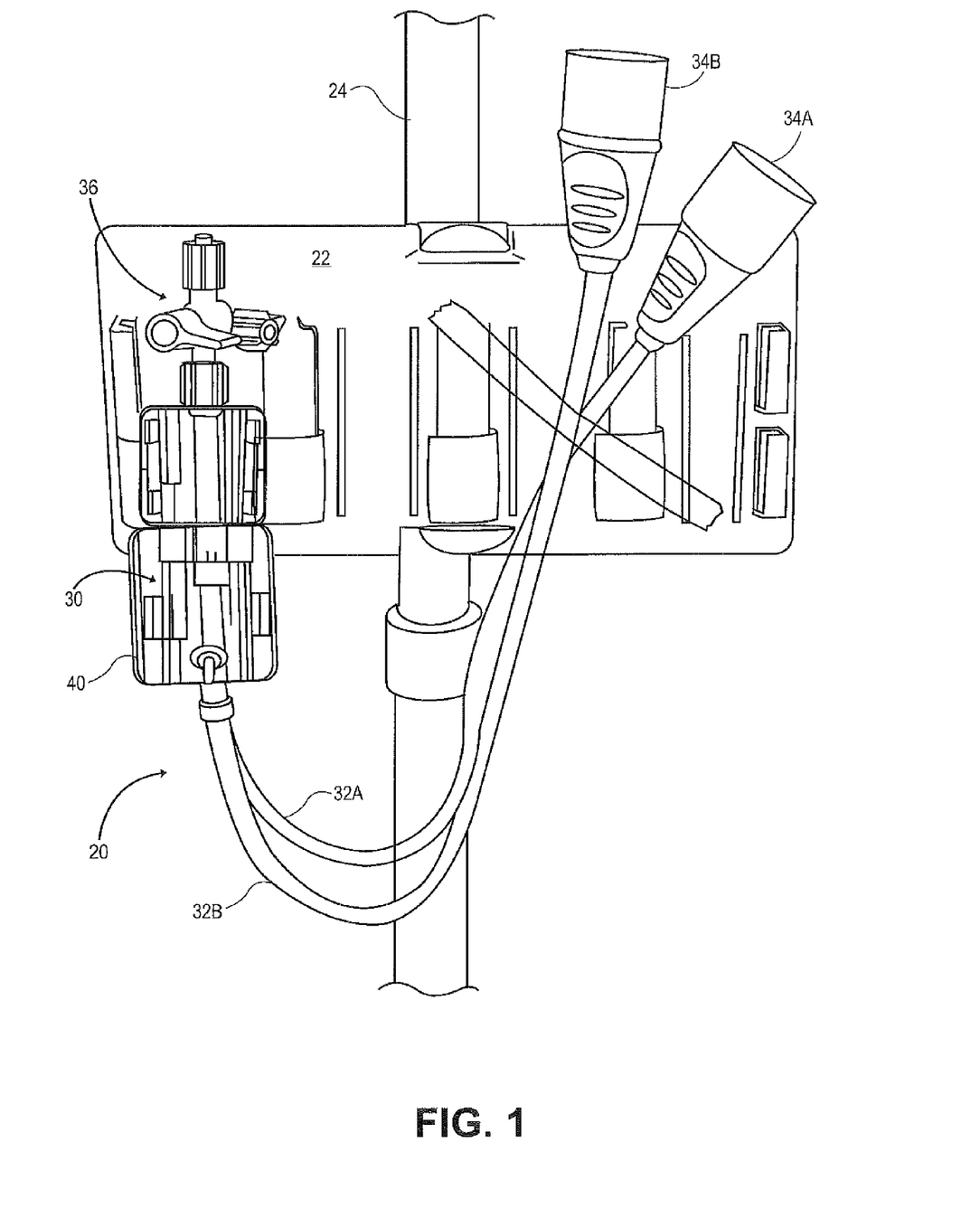
FIG. 1 is an elevational view of an exemplary disposable medical pressure transducing device of the present invention as typically mounted on a support pole for use.

Now with reference to FIGS. 1, 2 and 3A-3D, the main components of an exemplary disposable blood pressure transducing device (DPT) 20 will be described. FIG. 1 shows the DPT 20 mounted vertically to a mounting bracket 22 on a support pole 24, as is common in hospital settings. The DPT 20 includes a housing 30, a pair of cables 32a, 32b extending from one end of the housing and terminating in electrical connectors 34a, 34b, and a two-port stopcock assembly 36 on the opposite end of the housing. The DPT 20 is seen stretched out in a linear fashion in FIG. 2, and has an exemplary length from the farthest connector 34b to the stopcock assembly 36 of about 1 foot (30 cm), though longer cables may be used. Although not shown in these figures, an internal flow channel in the stopcock assembly 36 leads to a short length of tubing 38 situated on a top side of the housing 30 opposite a mounting plate 40. The mounting plate 40 engages L-shaped walls in the mounting bracket 22, as seen in FIG. 1, such that the tubing 38 faces outward from the mounting bracket.

Figure 2:
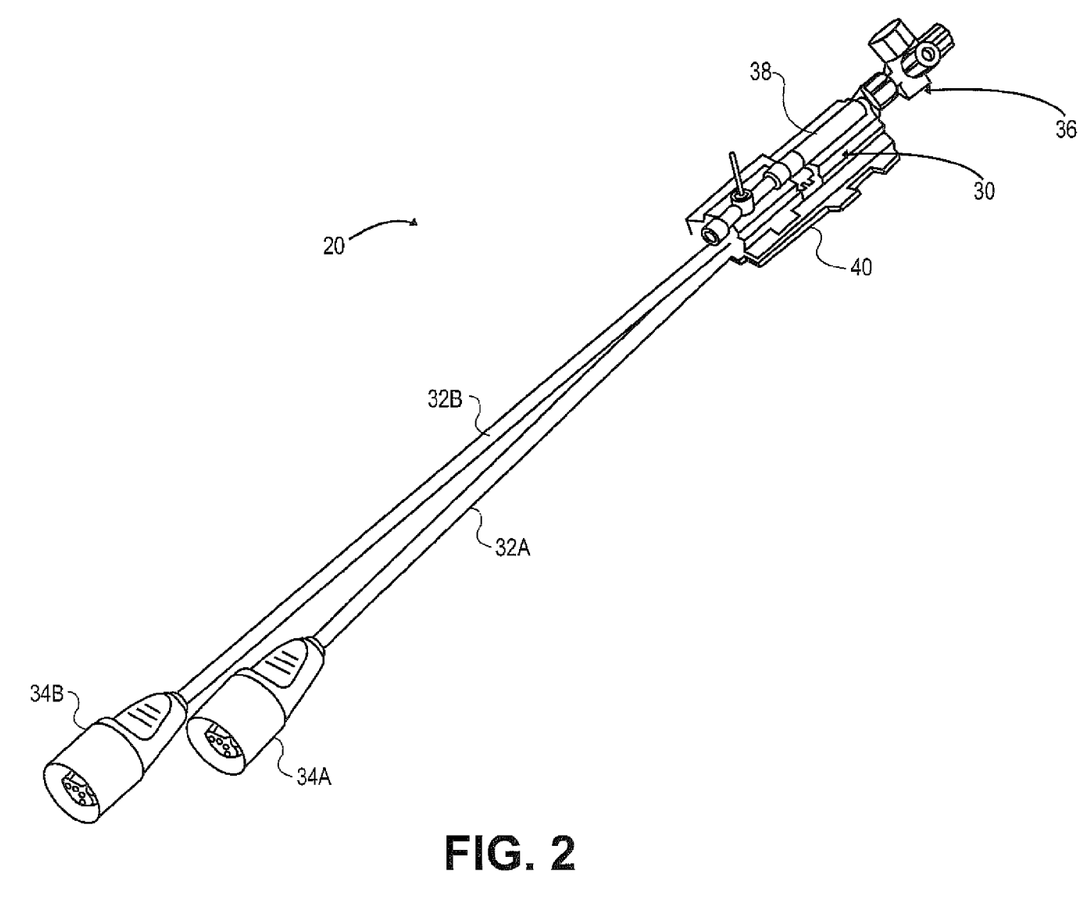
FIG. 2 is a perspective view of the exemplary disposable medical pressure transducing device with its cables stretched out straight.
Figures 3A, 3D:
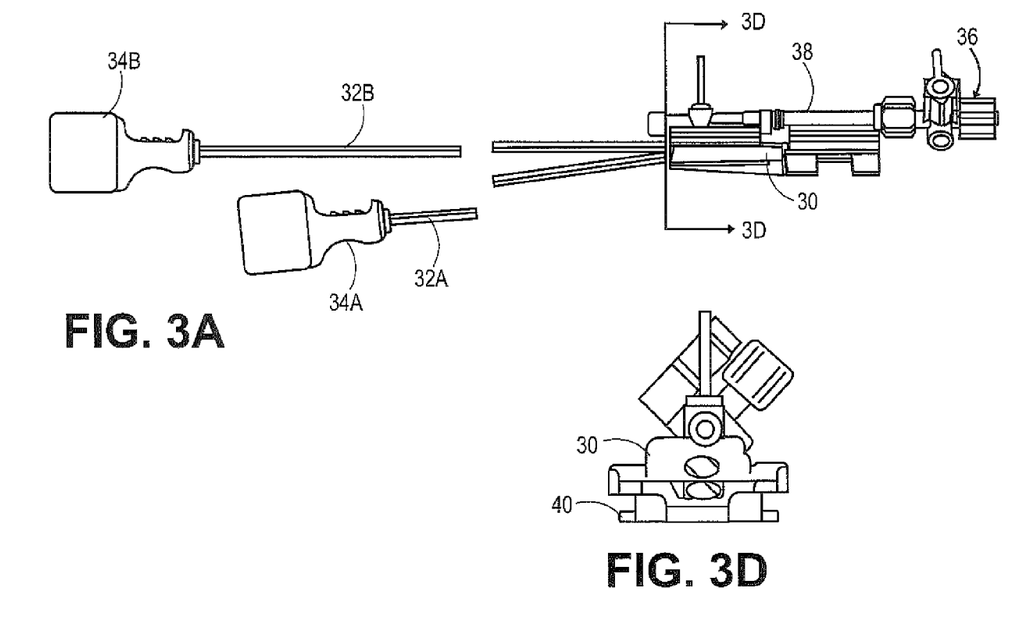
FIGS. 3A-3D are front, top, end and section views of the exemplary disposable medical pressure transducing device.
Figure 3B:
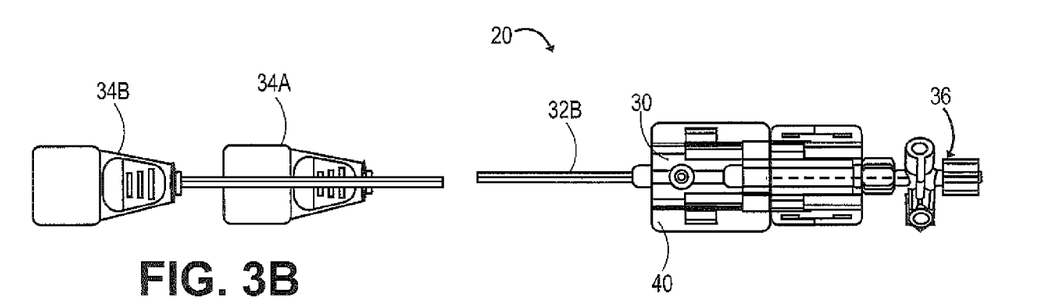
Figure 3C:
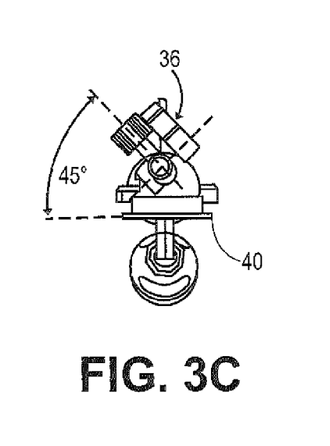

Not shown in FIGS. 1-3 are the associated components of the pressure monitoring system that connect to the DPT 20. Typically, a signal receiving device such as a patient or cardiac output monitor includes cables and connectors that mate with the connectors 34a, 34b and receive electrical signals indicative of fluid pressure detected by the DPT 20. Various monitors are available for this purpose and will not be further described herein, except below in the context of an interface feature of the present invention that permits identification by the monitor of the characteristics of the DPT 20. Additionally, an in-dwelling catheter that provides the particular fluid to be measured attaches to one of the ports of the stopcock assembly 36, typically the port in line with the DPT 20 that is fitted with a luer connector. Many catheters may be used for pressure monitoring, and the specifics are well known in the art. It should be noted, however, that the Edwards TruWave® Disposable Pressure Transducer is adapted to be combined with an arterial blood sampling line, such as the VAMP® (Venous Arterial Blood Management) kits also available from Edwards Lifesciences.

Furthermore, the term "catheter" as used herein refers to any elongated structure for accessing a body cavity such as a blood vessel and provides a conduit through which fluid may pass. In the preferred embodiment, a saline solution provides a fluid "column" through which pressure pulses from the catheter lumen are transmitted, and a pressure transducer positioned along the fluid column monitors those pressure pulses. Devices for providing such access include cannulas, needles, sheaths, introducers, and other such structures, typically tubular.

Figure 4:
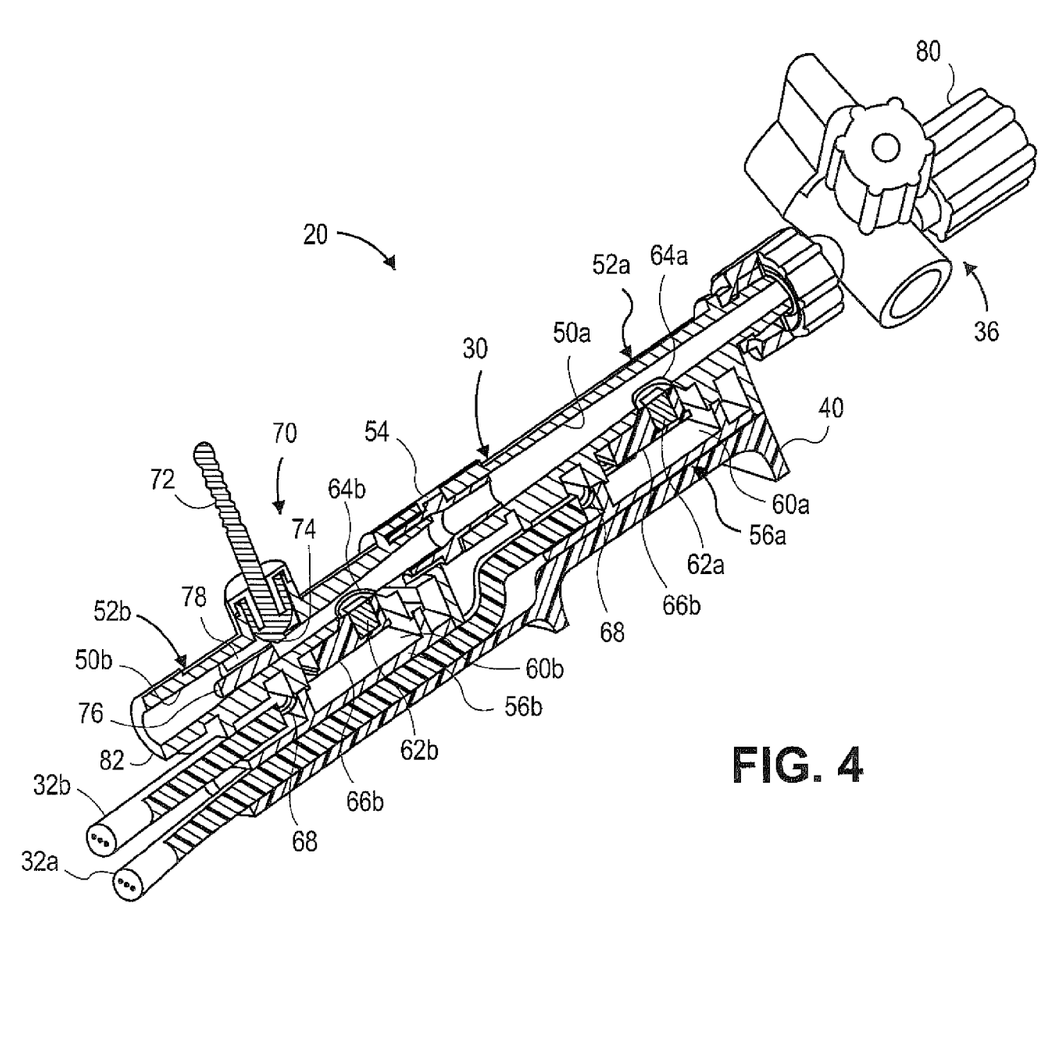
FIG. 4 is a longitudinal sectional view of a housing of the exemplary disposable medical pressure transducing device seen in perspective.
Figure 5:
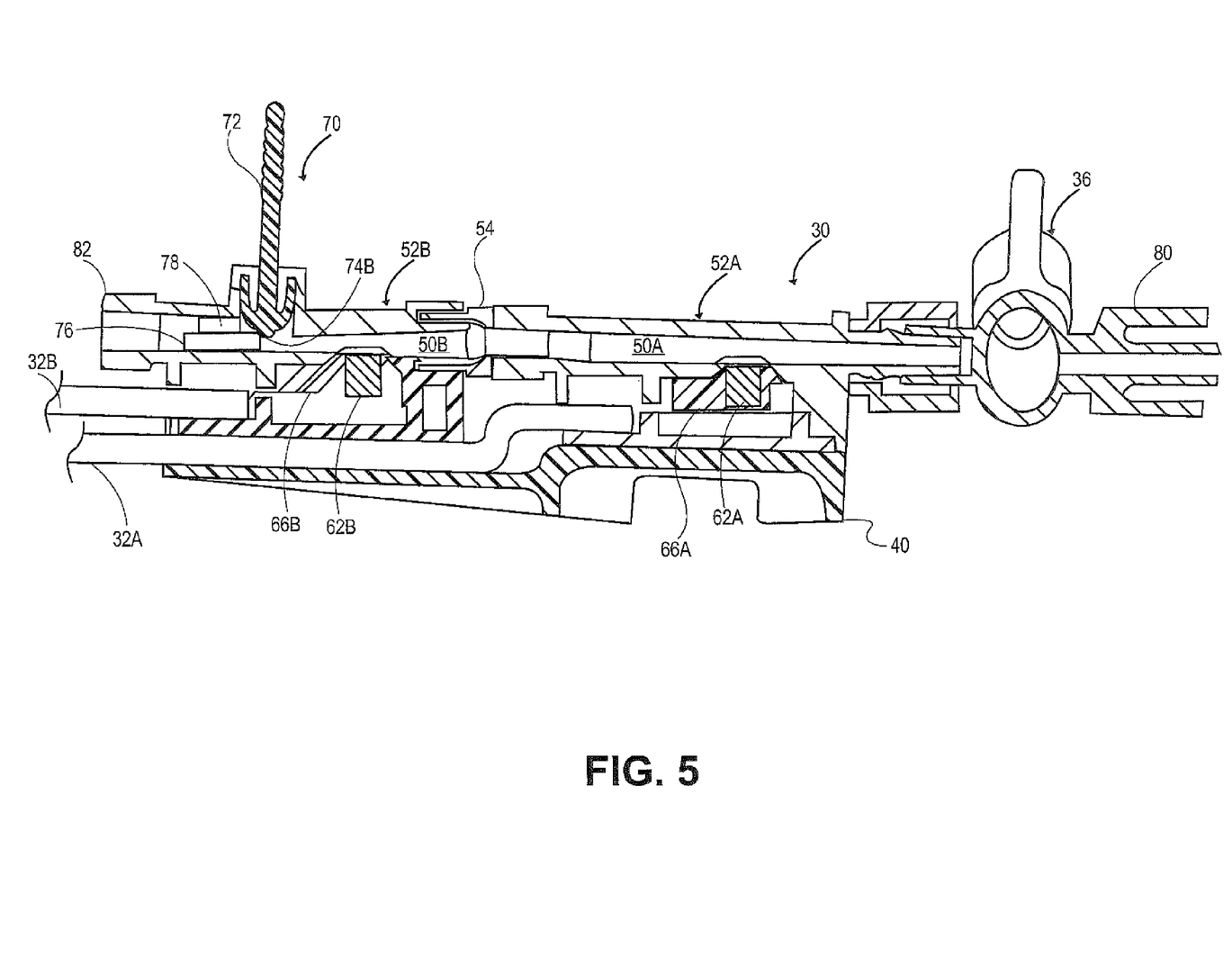
FIG. 5 is a longitudinal sectional view of a housing of the exemplary disposable medical pressure transducing device seen in elevation.

Now with reference to FIGS. 4 and 5, internal details of the DPT 20 are illustrated. The housing 30 actually comprises several components that are bonded or otherwise coupled together. The tubing 38 is formed by a first tube section 50a of a first manifold 52a, a second tube section 50a of a second manifold 52b, and a shunt member 54. A common lumen leads through the first and second tube sections 50a, 50b and shunt member 54. The housing 30 further includes first and second transducer enclosures 56a, 56b each having a large lower wall and a number of smaller walls upstanding therefrom that cooperate with and connect to oppositely-directed walls formed in the first and second manifolds 52a, 52b. The engaging walls may be bonded with adhesive or ultrasonic welding or the like. Each of these parts is typically made of molded medical grade plastic.

The first and second transducer enclosures 56a, 56b are substantially identical as is their respective cooperation with the first and second manifolds 52a, 52b. As a result, two similar transducer chambers 60a, 60b provide space for two pressure sensors or transducers 62a, 62b that are located adjacent openings 64a, 64b to the lumens of the first and second tube sections 50a, 50b, respectively. The transducers 62a, 62b mount in blocks 66a, 66b of insulating material and are placed in electrical communication with the cables 32a, 32b via wires 68. Fluid pressure within the common lumen of the housing tubing 38 can therefore be sensed at two closely spaced-apart locations. Because of the close spacing between the transducers 62a, 62b, typically no more than about 3 inches (8 cm), the two pressure waveforms being detected are not significantly different. Indeed, the stopcock assembly 36 is interposed between the housing conduit 38 and the in-dwelling catheter (not shown), and is opened to the atmosphere and providing a reference pressure in a saline fluid column defined within the conduit at a particular elevation. That is, as seen best in FIG. 1, the stopcock assembly 36 is normally positioned at the same elevation on the support pole 24 as the patient's heart. This equilibrates the "pressure heads" of the fluid column within the conduit 38 to that of the patient's heart. When the stopcock 36 is closed, the pressures sensed by the two pressure transducers 62 are the same along the fluid column in the conduit 38.

One particularly useful blood pressure transducer 62a, 62b is currently sold by Edwards Lifesciences of Irvine, Calif., under the trade name Edwards TruWave® Disposable Pressure Transducer, and includes a monolithic silicon pressure sensor employing a four-terminal resistive element formed in a thin monocrystalline silicon diaphragm. Acceptable silicon pressure sensors are commercially available from Motorola, Inc. More details on acceptable pressure transducers are disclosed in U.S. Pat. Nos. 4,539,998, and Re 33,518, the disclosures of both of which are hereby expressly incorporated herein by reference. A particularly preferred silicon pressure sensor is a sensor which includes a temperature compensation circuit for compensating the sensed pressure in the fluid based upon the temperature of the fluid and correcting such sensed pressure. Such a silicon pressure sensor is commercially available from Motorola, Inc. as SPX-1001D pressure sensors.

The first and second tube sections 50a, 50b are similarly sized but not identical because of the provision of a snap tab flush device 70 in the second. The snap tab flush device 70 includes a resilient tab 72 that has a distal end 74 normally occluding a port into the second tube section 50b. A plug 76 closes off the second tube section 50b adjacent the port, and the port leads to a by-pass channel 78. Pulling the tab 72 lifts the distal end 74 from the port and permits fluid to flow from the second tube section 50b to the by-pass channel 78. This flushes the device and also permits measurement of a square pressure wave created by the transient of the "snap" back of the tab 72. A square wave test pattern may be desirable for calibration of the transducers 62a, 62b.

The first and second tube sections 50a, 50b are in fluid-flow communication with an inlet port 80 provided on the stopcock assembly 36. The housing 30 further includes an outlet port 82. Both the inlet and outlet ports are structured to enable the affixing of tubing thereto and are axially aligned to provide a substantially unimpeded flow path through the housing 30. The inlet port 80, outlet port 82 and tubing 38 provide a fluid-flow pathway through which fluid can be administered to a patient while simultaneously permitting the monitoring of pressure waves along the fluid pathway.

In use, a catheter (not shown) is positioned within a body vessel or cavity and connected to intermediate tubing or directly to the inlet port 80. An I.V. set attaches to the proximal end of the catheter protruding from the patient so that a solution flows through the catheter and into the patient. Vents (not shown) in the first and second tube sections 50a, 50b permit an I.V. solution (typically saline) to fill the tube sections and provide a fluid "column" through which pressure pulses are transmitted. Connectors of one or more monitors (also not shown) are placed in communication with the transducers 62a, 62b via the electrical connectors 34a, 34b. Pressure measurements can then be taken as desired when the system is calibrated.

The provision of two transducers 62a, 62b and associated cables 32 and connectors 34 permits the DPT 20 to be connected to different monitors having different functions. For instance, a patient monitor that merely displays blood pressure can be connected to the first connector 34a and transducer 62a, while a cardiac output monitor may be connected to the second connector 34b and transducer 62b. The cardiac output monitor includes software that utilizes the pressure information in an algorithm that outputs cardiac volumetric flow data. In this way, a second DPT and second catheter is rendered unnecessary. Furthermore, some existing systems process a single pressure signal through both a patient monitor and a cardiac output monitor, which may be limited to a few selected patient monitors and increases pressure monitoring error through delays and distortion of the signal passed to the patient monitor. Further, the clinician must often ignore the Directions For Use of the patient monitor. It will be apparent therefore that the dual DPT 20 provides a significant tool to the critical care doctor.

As mentioned, the present invention provides an "identifier" in the DPT 20 that relays information to a connected signal receiving device such as a monitor concerning the characteristics or source of the DPT. This information can be used as a decision switch for overall functioning of the system, or can tell the monitor specific technical details about the DPT that aid in calibration and operation. In the context of disposable blood pressure transducers, the identifier permits the signal receiving device or monitor to appropriately condition the signal, which therefore helps improve safety. That is, various DPTs have different signal output characteristics depending on the type and physical specifications of the transducer, among other factors, and the signal typically requires amplification, filtering, and other such conditioning. Knowledge of the signal output characteristics via detection of the identifier instantly notifies the monitor of the proper conditioning to apply. It is conceivable that a monitor may be programmed to operate with numerous DPTs with different characteristics, requiring the monitor to apply different conditioning depending on the particular DPT. Of course, each DPT would have to have an identifier that can be detected by the monitor.

Figure 6:
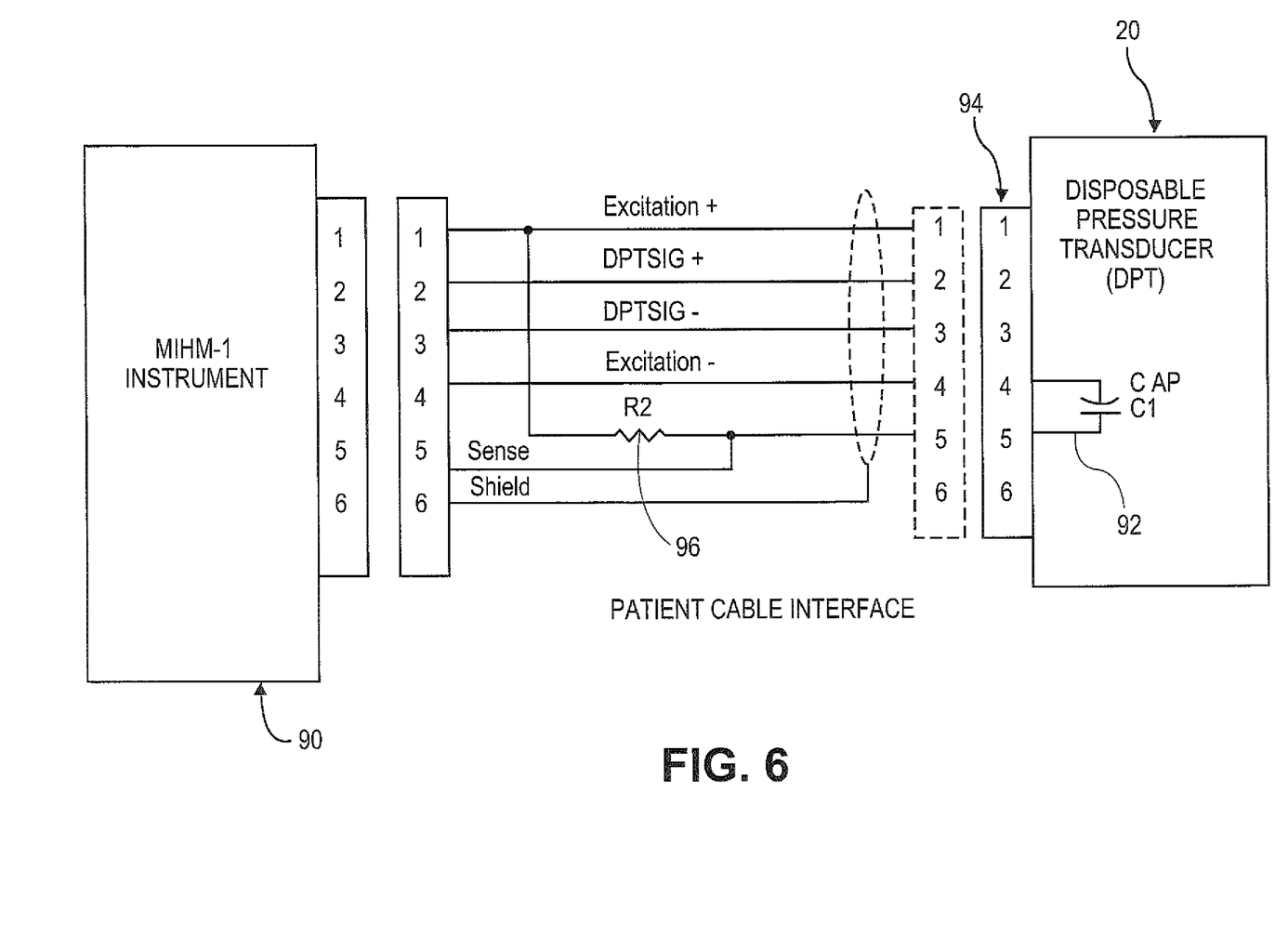
FIG. 6 is a circuit schematic of a connector pin interface between the exemplary disposable medical pressure transducing device and a signal receiving device.

FIG. 6 illustrates a schematic connector pin interface for the DPT 20 and an associated monitor 90 that enables the monitor to "see" whether the DPT is compatible, and determine the DPT characteristics. The exemplary "identifier" comprises a resistance/capacitance (RC) combination that possesses a characteristic time constant. Specifically, a capacitor 92 is connected between the $4^{th}$ and $5^{th}$ pins 94 of the DPT 20, a resistor 96 extends between an excitation pin 1 and pin 5. The monitor 90 includes software or other decision-making hardware that detects the time that it takes for the capacitor 92 in the RC circuit to charge. With an understanding of the specific resistance and capacitance values, the monitor 90 can decide whether the time equals an expected time, or falls within an acceptable time window, preferably about 20% plus or minus of the expected time. If the time to charge the capacitor 92 falls within the acceptable range, the system proceeds with the pressure monitoring. If not, the system shuts down and displays an error message, or otherwise indicates the non-compliance. Alternatively, the monitor 90 may include a programmed decision tree that processes the incoming pressure signals according to which type of DPT is detected, which is determined by the identifying time constant.

Numerous ways in which to incorporate an identifier into the DPT 20 are contemplated, all of which would require a complementary detector in the monitor 20. For instance, the identifier could be any combination of a resistor, a capacitor, and/or an inductor that is energized or interrogated by an electrical connection with the monitor to send an identifiable electric signal. These circuit components could reside in transducer 62 circuit itself, the cable 32, the connector 34, or even within the monitor 90. Alternatively, the identifier could comprise a memory chip (e.g., EEPROM) in the DPT 20 which is accessed by the monitor 90 upon electrical connection therebetween. More simply, the DPT 20 may contain a source of power such as a small battery which delivers a reference voltage/current to the monitor 90. It should be noted that the signature signal or modification of the standard DPT output could be time-based or frequency-based features that are recognizable by the monitor 90 (e.g., wireless auto-ID dot on DPT).

Other than circuit identifiers, an electro-magnetic signature inherent in a magnetic strip card, for example, could be used. In that case, the monitor 90 would require some mode of reading the strip card. Active or passive switches which can be electrically, mechanically, optically, or magnetically triggered (e.g. relays, FETs, transistors, switches), could also be used. For instance, a pressure switch in the monitor connector could be triggered by connection of the two connectors, whereas connection to a different DPT would not activate the switch. One specific example of such a switch is an insulated contact on the DPT 20 or monitor 90 connector that is pierced or broken and completes a circuit when the two connectors are engaged. Along the same lines, a scheme of optical identification via color, reflectivity, scattering, grating, or optochemical (e.g., barcode) may define the identifier.

Another desirable aspect of the present invention is the ability of the DPT 20 to produce two separate though identical pressure signals. This "dual DPT" enables pressure measurements from one arterial line to be simultaneously supplied to two separate monitoring devices (for example a patient monitor and a cardiac output monitor, or a patient monitor and an aortic balloon pump). This avoids the need to place another arterial line in the patient and connect another DPT for pressure monitoring, and reduces pressure monitoring error inherent in delays and distortion of signals that are supplied to a second monitor via the patient monitor.

In the exemplary embodiment, as seen in FIGS. 1-5, the dual DPT 20 includes two pressure transducers 62a, 62b within one housing 30, the transducers being fluid pressure sensors that directly sense blood pressure within a single length of tubing 38. Each transducer 62a, 62b has separate wires 68 extending therefrom and continuing in separate cables 32a, 32b that terminate in separate connectors 34a, 34b. One connector 34a, 34b can thus be placed in communication with a mating connector for a patient monitor and the other in communication with a mating connector for a cardiac output monitor. Preferably, only the assembly of the transducer 62, wires 68, cable 32, and connector 34 that communicates with the cardiac output monitor includes the "identifier" mentioned above, so that the monitor can detect the type of transducer and apply the proper signal conditioning. The connectors 34a, 34b may be differently colored to distinguish them and signify which one is associated with the identifier.

It should be understood that there are various ways to structure the DPT 20 to produce two output signals, and the present invention is intended to cover all such structures. For example, instead of the series configuration shown, the transducers 62a, 62b may be mounted in parallel with a bifurcation or "Y" in the fluid line. Alternatively, a single transducer assembly or manifold may be used with multiple sensors. Multiple sensors can be spaced axially in series along the fluid line, or at the same "height" around the circumference of the conduit. Circuitry may be provided to allow multiple instruments (input signals) to read one sensor (e.g. multiplexing or signal matching). In all these cases it should be understood that the sensors are external to the body and not mounted on the in-dwelling catheter. Furthermore, as mentioned above, the sensors may or may not be fluid pressure transducers, and may or may not directly measure blood pressure. One specific alternative is a dual optical sensor that senses blood pressure from a distinct pulse point where the arteries are near enough to the surface of the skin, such as in the neck or wrist.

While the foregoing is a complete description of the preferred embodiments of the invention, various alternatives, modifications, and equivalents may be used. Moreover, it will be obvious that certain other modifications may be practiced within the scope of the appended claims.

What is claimed is:

1. A disposable blood pressure transducing apparatus comprising:
   a housing;
   a first pressure-sensitive transducer mounted on the housing and configured to measure a patient's blood pressure and to convert the measured pressure to a corresponding first electrical pressure signal;
   an identifier including electrical circuitry configured to provide an identifier signal associated with the pressure transducing apparatus, the identifier signal identifying the pressure transducing apparatus by reaching a predetermined value within a prescribed time window; and
   a first electrical connector mounted on the housing and including a plurality of electrical conductors, wherein a first conductor is configured to transmit the first pressure signal and a second conductor is configured to transmit the identifier signal;
   wherein the first electrical connector is configured to be connectable to a monitoring instrument that receives and processes the first pressure signal and the identifier signal to determine the patient's blood pressure.

2. A disposable blood pressure transducing apparatus as defined in claim 1, wherein the identifier is mounted at least in part on the housing.

3. A disposable blood pressure transducing apparatus as defined in claim 2, wherein the electrical circuitry of the identifier includes a resistance/capacitance (RC) combination having a characteristic time constant.

4. A disposable blood pressure transducing apparatus as defined in claim 3, wherein:
   the blood pressure transducing apparatus further comprises a cable interface having a second electrical connector configured to be connectable to the first electrical connector; and
   the identifier includes a capacitor mounted on the housing and a resistor mounted on the cable interface.

5. A disposable blood pressure transducing apparatus as defined in claim 1, wherein:

the housing includes a conduit for receiving the patient's blood; and the first pressure-sensitive transducer is mounted on the housing, in fluid communication with the conduit.

6. A disposable blood pressure transducing apparatus as defined in claim 5, wherein:

the blood pressure transducing apparatus further comprises a second pressure-sensitive transducer configured to measure the patient's blood pressure and to convert the measured pressure to a corresponding second electrical pressure signal;

the second pressure-sensitive transducer is mounted on the housing, in fluid communication with the conduit, at a location spaced apart from the first pressure-sensitive transducer; and the first electrical connector further includes a third conductor configured to transmit the second pressure signal.

7. A disposable blood pressure transducing apparatus as defined in claim 6, and further comprising:

a first cable configured to transmit the first pressure signal; and a second cable configured to transmit the second pressure signal;

wherein the first and second cables are configured to be connectable to separate monitoring instruments.

* * * * *